United States Patent
Theyssen et al.

(10) Patent No.: US 8,119,578 B2
(45) Date of Patent: Feb. 21, 2012

(54) METHOD OF LUBRICATING A CONVEYOR SYSTEM

(75) Inventors: Holger Theyssen, Freinsheim (DE); Stefan Grober, Frankensthal (DE)

(73) Assignee: Diversey, Inc., Sturtevant, WI (US)

( * ) Notice: Subject to any disclaimer, the term of this patent is extended or adjusted under 35 U.S.C. 154(b) by 713 days.

(21) Appl. No.: 11/720,863

(22) PCT Filed: Dec. 15, 2005

(86) PCT No.: PCT/US2005/045747
§ 371 (c)(1), (2), (4) Date: Nov. 4, 2008

(87) PCT Pub. No.: WO2006/066120
PCT Pub. Date: Jun. 22, 2006

(65) Prior Publication Data
US 2009/0253598 A1    Oct. 8, 2009

(30) Foreign Application Priority Data
Dec. 27, 2004 (EP) ................... 04030791

(51) Int. Cl.
*C10M 171/00* (2006.01)
*F16N 7/00* (2006.01)
(52) U.S. Cl. .................... 508/110; 184/15.1
(58) Field of Classification Search ........... 508/110; 184/15.1
See application file for complete search history.

(56) References Cited

U.S. PATENT DOCUMENTS

| | | | | |
|---|---|---|---|---|
| 3,699,348 | A * | 10/1972 | Hocherl | 250/576 |
| 4,604,220 | A | 8/1986 | Stanton et al. | |
| 4,666,858 | A | 5/1987 | Magnuson et al. | |
| 5,419,837 | A | 5/1995 | Godfrey et al. | |
| 5,935,914 | A | 8/1999 | Theyssen et al. | |
| 6,464,798 | B1 | 10/2002 | Rosenbauer et al. | |
| 2002/0115574 | A1* | 8/2002 | Li et al. | 508/208 |
| 2003/0058450 | A1 | 3/2003 | Mosley et al. | |
| 2004/0013221 | A1 | 1/2004 | Elkins | |

FOREIGN PATENT DOCUMENTS

| | | |
|---|---|---|
| DE | 2328328 | 12/1974 |
| DE | 4234466 | 4/1994 |
| DE | 9420305 | 3/1995 |
| EP | 0044458 | 1/1982 |
| EP | 0533552 | 3/1993 |
| EP | 0559305 | 9/1993 |
| EP | 0564948 | 10/1993 |
| EP | 0614079 | 9/1994 |
| EP | 1192860 | 4/2002 |
| EP | 1192860 A1 * | 4/2002 |
| GB | 1309551 | 3/1973 |

OTHER PUBLICATIONS

The International Search Report from the European Patent Office.
Written Opinion Received in PCT/US2005/045747, May 30, 2006.
Office Action received in EP Application No. 04030791, Apr. 16, 2007.
Office Action received in EP Application No. 04030791, Nov. 21, 2007.
Office Action received in EP Application No. 04030791, Jul. 29, 2008.
Notice of Intention to Grant European Patent received in EP Application No. 04030791, Jan. 4, 2011.
International Search Report from the European Patent Office, Jun. 22, 2006.

* cited by examiner

*Primary Examiner* — Walter D Griffin
*Assistant Examiner* — Taiwo Oladapo
(74) *Attorney, Agent, or Firm* — Gregory S. Bollis

(57) ABSTRACT

The present invention is directed to a method of lubricating a conveyor system comprising
  i) diluting a conveyor lubricant concentrate with water to obtain an aqueous conveyor lubricant with the concentration c,
  ii) irradiating an aqueous conveyor lubricant with light,
  iii) determining the concentration c of the aqueous conveyor lubricant by measuring the absorption of the light by the aqueous conveyor lubricant with an absorption detector and
  iv) applying the aqueous conveyor lubricant to the conveyor system.

The present invention further relates to a conveyor lubrication system including a measuring device with a light source and with an absorption detector for measuring the absorption of light by an aqueous conveyor lubricant within a conveyor lubrication system.

20 Claims, 6 Drawing Sheets

METHOD OF LUBRICATING A CONVEYOR SYSTEM

FIELD OF THE INVENTION

The invention relates to methods and systems for lubricating conveyor systems. More specifically, the invention relates to lubricating conveyor systems, which are moving containers made of metal, glass, paper, cardboard and/or plastic, particularly containers used in the food industry. These are especially containers to be filled up with food including beverages, e.g. glass or plastic bottles, boxes, glasses, vessels, beverage containers, paper and cardboard holders and the like.

BACKGROUND OF THE INVENTION

The application of aqueous conveyor lubricants for lubricating and possibly also cleaning and disinfecting conveyor systems, specifically for lubricating the interface between a container and a moving conveyor belt or track surface, is well known in prior art. If a conveyor system is not lubricated sufficiently, this can lead to the falling down of the containers or have the result that the containers do not stop, even though they have reached a filling, cleaning or labelling station. Both kinds of malfunctions can lead to longer standing times of the conveyor system and to a considerable loss of capacity.

Aqueous conveyor lubricants are usually applied in very low concentrations e.g. in a range from 0.1% to 2%, while the necessary quantity of aqueous conveyor lubricant is high. The exact determination of concentration of the applied lubricants is of a high significance, in order to guarantee an optimal lubrication of the conveyor system.

Presently the concentration of aqueous conveyor lubricants is determined by manually retaining a sample of the conveyor lubricant and examining it by titration. This method is very inaccurate, due to the difficult recognition of the equilibrium point during the titration. Furthermore, this analysis technique takes a long time to obtain results and is not adapted for an on-line application.

The present invention seeks to avoid these disadvantages by proposing a technique of measuring by a spectro-photometric method, particularly by the absorbance of light, which is simpler, faster and easier to implement than the laboratory method discussed above. Furthermore, this method can be adapted to use on-line.

Many molecules absorb ultraviolet or visible light. Lambert-Beer's Law is a mathematical means of expressing how light is absorbed by matter. The Law states that the amount of light emerging from a sample is diminished by three physical phenomena:

1. The amount of absorbing material in its path length (concentration)
2. The distance the light must travel through the sample (optical path length)
3. The probability that the photon of that particular wavelength will be absorbed by the material (absorptivity or extinction coefficient). This relationship may be expressed as:

$$A = ebc$$

were
A=absorbance
e=molar extinction coefficient
b=path length in cm and
c=molar concentration.

Different molecules absorb radiation of different wavelength. An absorption spectrum will show a number of absorption bands corresponding to structural groups within a molecule. An absorption spectrum shows the absorption of light as a function of a wavelength.

The determination of a concentration by measuring the absorption of light is a modern, reliable and competitive method, which is applied especially for industrial waste-water analysis.

Examples for the concentration detection of a component of an industrial water system can be found in U.S. Pat. No. 5,419,837 or in US 2004/013221 A. U.S. Pat. No. 4,666,858 teaches the determination of the quantity of anionic material in electrolyte metal plating baths by spectro-photometrical measuring the ultraviolet absorption of the extracted material.

DE-A1 42 34 466 is directed to a method for the determination of the concentration of a substance within a solution. This document teaches the use of a tracer, which is a fluorescence dye, the concentration of which is measured by an optical method.

An object of the present invention is to provide a method of lubricating a conveyor system, which assures an optimal concentration of the applied lubricant.

Another object of the present invention is to make a conveyor system more efficient by avoiding standing times and increasing its transport capacity. Another object of the present invention is to permit the on-line determination of the concentration of an aqueous conveyor lubricant, which is applied to a conveyor system.

SUMMARY OF THE INVENTION

These and other objects are achieved by the present invention, which comprises a method of lubricating a conveyor system comprising
  i) irradiating an aqueous conveyor lubricant having a concentration c with light,
  ii) determining the concentration c of the aqueous conveyor lubricant by measuring the absorption of the light by the aqueous conveyor lubricant with an absorption detector and
  iii) applying the aqueous conveyor lubricant to the conveyor system.

This automated procedure allows exact dosage of applied lubricants and the concentration measurement to be integrated directly into the lubrication process. The invention provides a secure lubrication process, avoiding unnecessary over-concentration of the lubricant and therefore avoiding high product costs. The concentration of the lubricant has to be observed e.g. if the aqueous conveyor lubricant is not stable or if the conveyor lubricant is diluted prior to application and the diluting process is not constant or reliable. Furthermore, if the tank containing the conveyor lubricant concentrate or the aqueous conveyor lubricant is nearly empty, the attention of an operator has to be called to the resulting drop in concentration. The conveyor lubrication system of the present application can be equipped with an alarm device, which raises an alarm signal if an unwanted concentration of the aqueous conveyor lubricant is determined.

If the conveyor lubricant is delivered to the conveyor lubrication system in a concentrated form, the conveyor lubricant concentrate can be diluted with water to obtain an aqueous lubricant with a concentration c, before carrying out steps i) to iii) of the method according to the invention. If the conveyor lubricant is already delivered in the desired concentration c, this diluting step is not necessary.

The present invention further refers to a conveyor lubrication system including an application device for applying an aqueous conveyor lubricant to a conveyor system. The conveyor lubrication system further includes a measuring device with a light source and with an absorption detector for measuring the absorption of light by the aqueous conveyor lubricant within the conveyor lubrication system.

The present invention further refers to another conveyor lubrication system, including a dosing station and an application device, the dosing station containing at least one dosing pump for pumping a conveyor lubricant concentrate through a dosing pipe into at least one mixing space. The mixing space is attached to a water supply for diluting the conveyor lubricant concentrate with water within the mixing space to obtain an aqueous conveyor lubricant. The mixing space is attached to at least one outlet pipe for transporting the aqueous conveyor lubricant out of the mixing space. The outlet pipe is leading to the application device for applying the aqueous conveyor lubricant to a conveyor system. The conveyor lubrication system further includes a measuring device with a light source and with an absorption detector for measuring the absorption of light by the aqueous conveyor lubricant within the conveyor lubrication system.

DESCRIPTION OF VARIOUS AND PREFERRED EMBODIMENTS

Figure 1:
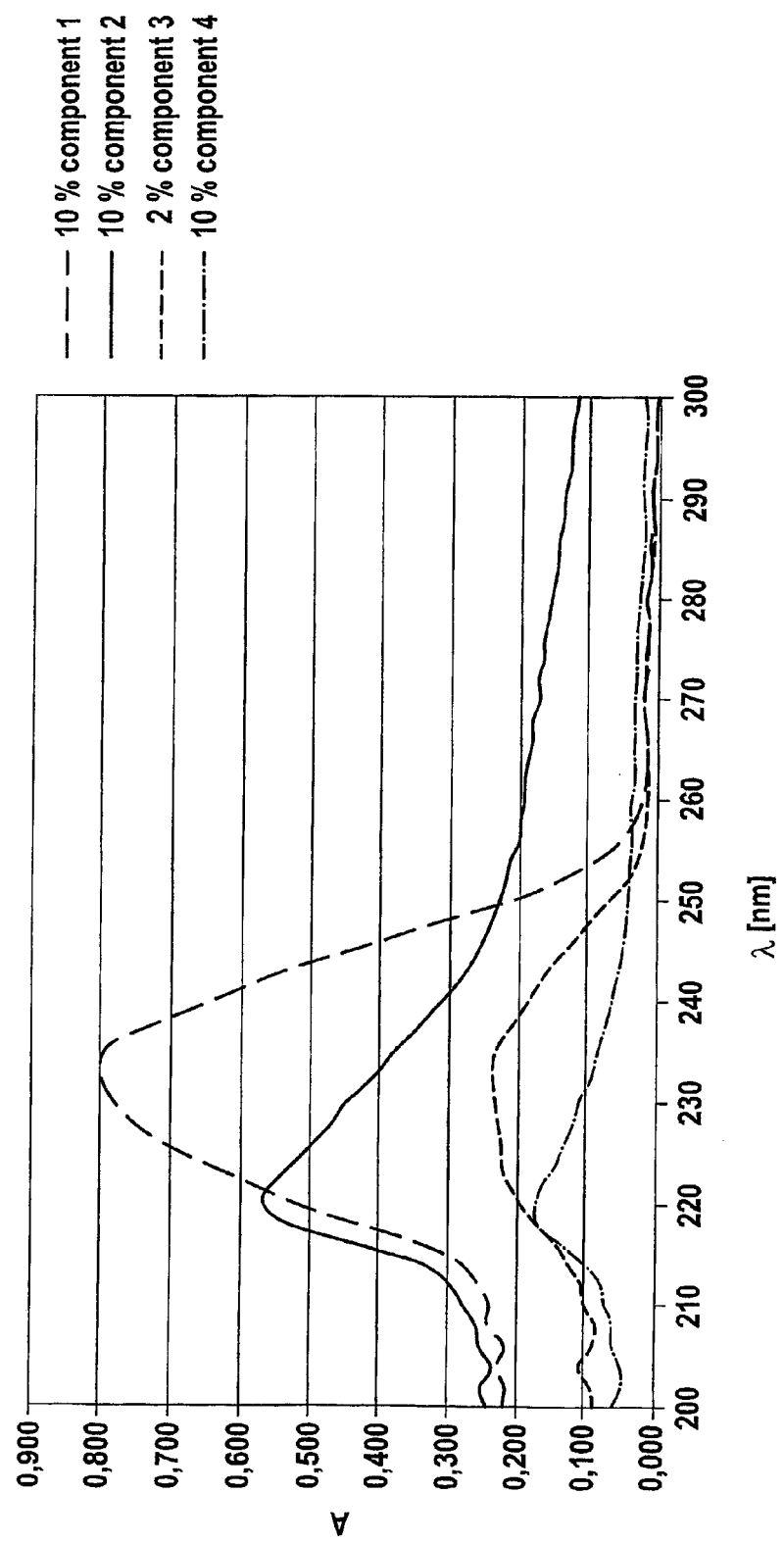
FIG. 1 shows absorbance spectra of different aqueous solutions containing components of conveyor lubricants, plotting absorbance versus wavelength

The method of the present invention is concerned with lubricating a conveyor system. Conveyor systems are systems for transporting goods in industrial plants, comprising conveyor belts, conveyor bands, conveyor lines, tracks and the like.

According to the proposed method, if the lubricant is available in a concentrated form, the conveyor lubricant concentrate is diluted with water to obtain an aqueous conveyor lubricant. This dilution step of a concentrate is necessary, since the lubricant is applied to the conveyor system with a low concentration.

Examples of conveyor lubricant concentrates and aqueous conveyor lubricants can be found in EP 0946 692 B1, the disclosure of which is incorporated herein by reference. This European patent refers to lubricants on the basis of soap, on the basis of fatty amines and on the basis of phosphate esters. The present invention is mainly directed to lubricants on the basis of amines and on the basis of soap and furthermore to lubricants on the basis of ether carboxylic acid.

Preferably the conveyor lubricant concentrate is diluted with water to obtain an aqueous conveyor lubricant with a concentration c in a range from 0.05 to 2.5%, particularly in a range from 0.1% to 0.3% referring to lubricants on the basis of amines, ether carboxylic acids or ethoxylate and particularly in a range from 0.5 to 2% referring to lubricants on the basis of soap. All percentages referred to in this context are percentages by weight.

If the aqueous conveyor lubricant is available with the desired concentration c, the diluting step is unnecessary.

According to the present invention the aqueous conveyor lubricant is irradiated with light, the absorption of the light by the lubricant being measured with a light detector. For the irradiation a light source is used, preferably a light source selected from the group of a hydrogen lamp, a deuterium lamp, a laser and a tungsten lamp. Preferably the aqueous conveyor lubricant is irradiated with visible or ultraviolet light of one specific wavelength. This wavelength is advantageously the wavelength of an absorption peak of a component of the aqueous conveyor lubricant. If the used light source is a continuous light source, emitting light in a range of wavelength, the desired specific wavelength for irradiating the lubricant can be selected by a wavelength separator, e.g. a prism, a grating or a monochromator.

According to one preferred embodiment of the present invention, the absorption of light with a wavelength in a range from 200 to 300 nm is measured.

The light from the light source is focused and sent into the aqueous conveyor lubricant within an element of the conveyor lubrication system, e.g. within a pipe or chamber of the dosing station. The emerging light, which has penetrated the aqueous conveyor lubricant is measured on the opposite side of the element by an absorption detector. The absorption detector includes for example a photo-electric cell, a photo-diode or a photo-multiplier. The detector is usually connected with an amplifier and a data processing unit. The measured absorbance is compared to a calibration curve (e.g. by the data processing unit) to determine the concentration of the lubricant. The calibration curve shows the absorbance as a function of the concentration for this aqueous lubricant (according to the Lambert-Beer-Law) at the chosen wave length and with the used set-up. The calibration curve has been determined by measuring the absorbance of the same lubricant of known concentrations with the same set-up.

According to a preferred embodiment of the present invention, the absorption of the light is measured on-line during operation of the conveyor system. Preferably the measured concentration values are used to control the application quantity of the aqueous conveyor lubricant. The on-line measurement of the concentration permits a fast response to unwanted concentration variations by varying the application quantity of lubricant to the conveyor system. Another possibility would be controlling the amount of water mixed with the conveyor lubricant concentrate or the amount of conveyor lubricant concentrate mixed with the water in the diluting step, depending on the determined concentration of the aqueous conveyor lubricant.

According to the present invention, the aqueous lubricant is applied to the conveyor system. The conveyor system is automatically and continuously lubricated by a conveyor lubrication system according to the present invention.

Preferably the aqueous conveyor lubricant is applied to the conveyor system by spraying, brushing or dipping. The spraying can be carried out by spraying nozzles, the brushing by brushes and the dipping by leading the conveyor band through dip trays, which contain the aqueous conveyor lubricant.

The conveyor lubrication system preferably includes a dosing station and an application device. The dosing station doses the amount of conveyor lubricant concentrate and the amount of water, which are mixed in order to obtain the aqueous conveyor lubricant with a concentration c. The application device serves to apply the lubricant to the conveyor system, including for example spraying nozzles for a spray application. For measuring the absorption of light as described above, the conveyor lubrication system further contains a measuring device.

According to a preferred embodiment of the present invention, the measuring device of the conveyor lubrication system includes a flow cell, which is equipped with the light source and the absorption detector and which is connected to an element of the dosing station or the application device, the element containing the aqueous conveyor lubricant. The flow cell can be connected for example to a pipe or a mixing chamber of the dosing station or the application device, through which the aqueous conveyor lubricant is flowing during the operation of the conveyor lubrication system.

FIG. 1 represents absorbance spectra of different aqueous solutions containing components of conveyor lubricants, plotting absorbance A versus wavelength λ.

The absorbance spectra were measured by scanning a wavelength separator over the wavelength range from 200 nm to 300 nm. A first aqueous solution contained the component 1, which was an alkyl (C16-18) ether (9 EO) carboxylic acid, with a concentration of 10%. The absorbance spectrum of this aqueous solution with the component 1 shows an absorption maximum at about λ=234 nm.

A second aqueous solution contained the component 2, which was N-oleyl-1,3-diamino propane, with a concentration of 10%. The absorbance spectrum of this aqueous solution with component 2 shows an absorption maximum at about λ=220 mm.

A third aqueous solution contained the component 3, which was oleylamine ethoxylate (12 EO), with a concentration of 2%. The absorbance spectrum of this aqueous solution with the component 3 shows an absorption maximum at about λ=234 nm.

A fourth aqueous solution contained the component 4, which was N-coco-1,3-diamino propane, with a concentration of 10%. The absorbance spectrum of this aqueous solution with the component 4 shows an absorption maximum at about λ=220 nm.

The four components 1 to 4 are typical components of aqueous conveyor lubricants. An optimum wavelength for an ultraviolet absorption detection using lubricants containing at least one of these components is the wavelength of the absorption peaks in FIG. 1, i.e. 220 nm or 234 nm.

According to a preferred embodiment of the present invention the concentration c of the aqueous conveyor lubricant is determined my measuring the absorption of ultraviolet light of a specific wavelength, the ultraviolet light being primarily absorbed by at least one lubricant component of the aqueous conveyor lubricant, the lubricant component being a component selected from the group of an amine, an ether carboxylic acid and an sulfonate. The amine is preferably used in the form of an acetate.

Preferred amines which could be a lubricant component according to the invention are those corresponding to the general formula I, as well as salts thereof,

(I)

wherein $R^6$, $R^7$, $R^8$ and $R^9$ independently from each other are the same or different and indicate:

hydrogen a substituted or unsubstituted, linear or branched alkyl rest with 1 to 22 C-atoms or a mono or polyunsaturated alkenyl rest with 2 to 22 C-atoms, which could display as substituents one or more hydroxyl, amine, imine, halogen and/or carboxyl rests, a substituted or unsubstituted phenyl rest, which could display as substituents one or more amine, imine, hydroxyl, halogen, carboxyl and/or possibly again substituted, linear or branched, saturated or mono or polyunsaturated alkyl rest with 1 to 22 C-atoms, $A^2$ indicates a linear or branched alkylene group with 1 to 8 carbon atoms, and n is a positive integer number in the range of 1 to 30.

Preferred amines are of the general formula I, wherein
$R^7$, $R^8$ and $R^9$=hydrogen
$A^2$=—$(CH_2)_3$—, and
n=1.

Also the salts of those compounds which belong to the following general formulas (II) and (III) can be preferably applied, $$R^6-NH-(CH_2)_3N^+H_3X^-$$ (II)

$$R^6-{}^+NH_2-(CH_2)_3N^+H_32X^-$$ (III), wherein $R^6$ has the meaning as mentioned for the formula I and
wherein the anion $X^-$ is chosen from all the customary rests, which are familiar to the professional, which originate from inorganic acids, organic acids and which do not influence the lubricant concentrate according to the invention in a detrimental manner, for example do not result in undesired turbidity or standstills, can be applied.

In the sense of the present invention such acids are preferred of which the anion $X^-$ is chosen from the group: amidosulphonate, nitrate, halide, hydrogensulphate, sulphate, hydrogencarbonate, carbonate, phosphate or $R^5$—$COO^-$ whereby the rest $R^5$ indicates hydrogen, a substituted or unsubstituted, linear or branched alkyl rest with 1 to 20 C-atoms, whereby the substituents are chosen from one or more hydroxyl, amine, imine and/or carboxyl rests. Especially mentioned as examples for the organic anions $X^-$ of the type $R^5$—$COO^-$ are: formate, acetate, glycolate, oleate, lactate, gluconate, citrate and glutamate. In another embodiment of the present invention, preferred amines can also be obtained according to the general formula I, wherein
$R^6$ is a saturated or unsaturated, branched or linear alkyl group with 8 to 22 carbon atoms,
$R^7$ is hydrogen, an alkyl group of hydroxyl-alkyl group with 1 to 4 carbon atoms or $A^2$-$NH_2$,
n=1 and $R^8$ and $R^9$ indicate hydrogen.

Some individual examples of amines which could be applied according to the invention are among others ethylene diamine, diethylene triamine, triethylene tetra-amine, propylene diamine, dipropylene triamine, tripropylene tetra-amine, butylene diamine, aminoethyl propylene diamine, aminoethyl butylene diamine, tetramethylene diamine, hexamethylene diamine, N-coco-1,3-diamonopropane, (N-cocos fatty-alkyl-1,3-diaminopropane) N-tallow fatty-alkyl-1,3-diaminopropane (N-oleyl-1,3-diaminopropane), N-lauryl-1,3-diaminopropane, each time in the form of the free amine or in the form of the salt like formate, acetate, oleate, glycolate, lactate, gluconate, citrate, glutamate, benzoate or salicylate.

More preferred polyamines are N-coco-1,3-diaminopropane and N-oleyl-1,3-diaminopropane, the most preferred polyamine is N-oleyl-1,3-diaminopropane.

Compounds according to the general formulas IV and V can also be applied as an amine component:

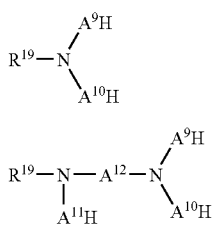

wherein
$R^{19}$ is a linear or branched, saturated or unsaturated, alkylene rest with 8 to 22 carbon atoms,
$A^{12}$ is a linear or branched alkylene group with 8 to 22 carbon atoms,
$A^9, A^{10}, A^{11}$ are the same or different ethoxy or propoxy groups, whereby the total of the groups $A^9, A^{10}, A^{11}$ is between 2 and 200.

Useful compounds among others are:
Cocos-bis(2-hydroxylethyl)amine, polyoxyethylene (5) cocos-amine, polyoxyethylene (15) cocos-amine, tallow-bis(2-hydroxylethyl)amine, polyoxyethylene(5) tallow-amine, tallow/oleyl-bis(2-hydroxylethyl)amine, oleyl-bis(2-hydroxylethyl)amine, polyoxyethylene (5) oleylamine, polyethylene (15) oleylamine, tallow-bis(2-hydroxylethyl)amine (hydrated), polyoxyethylene (5) tallow-amine (hydrated), polyoxyethylene (15) tallow-amine (hydrated), polyoxyethylene (50) tallow-amine, N,N'N'-tris(2-hydroxylethyl)N-tallow-1,3-diaminopropane, N,N',N'-polyoxyethylene (10)-N-tallow-1,3-diaminopropane, N,N',N'-polyoxyethylene (15)-N-tallow-1,3-diaminopropane and poly oxyethylene (15)-tallow-amine Preferred ether carboxylic acids which could be a lubricant component according to the invention are those corresponding to the general formula VI, $$R^{20}-(O(CH_2)_m)_nOCH_2COO^-M^+ \quad (VI)$$

wherein
$R^{20}$ is a saturated, linear or branched alkyl rest with 1 to 22 carbon atoms or a mono or polyunsaturated linear or branched alkaryl or alkinyl rest with 2 to 22 carbon atoms or a possibly mono or poly $C_1$-$C_{22}$ alkyl or $C_2$-$C_{22}$ alkenyl or $C_2$-$C_{22}$-alkinyl substituted aryl rest n is a positive number between 0 and 30, and m is 2 or 3,
M is hydrogen or an alkali metal.

As ether carboxylic acids with the general formula VI, which can be applied advantageously, can be mentioned among others:

| $R^{20}$ | n | CTFA-name |
|---|---|---|
| Lauryl | 2-5 | Laureth-4 carboxylic acid |
| Lauryl | 3-8 | Laureth-5 carboxylic acid |
| Lauryl | 4-5 | Laureth-6 carboxylic acid |
| Lauryl | 10 | Laureth-11 carboxylic acid |
| Lauryl | 13 | Laureth-14 carboxylic acid |
| Oleyl | 5 | Oleth-6 carboxylic add |
| Oleyl | 9 | Oleth-10 carboxylic acid |
| Octylphenol | 8 | Octoxynol-9 carboxylic acid |
| Octylphenol | 19 | Octoxynol-20 carboxylic acid |
| Norylphenol | 0 | Nonoxynol-carboxylic acid |
| Norylphenol | 7 | Nonoxynol-8 carboxylic acid |
| Stearyl | 6 | Steareth-7 carboxylic acid |
| Stearyl | 10 | Steareth-11 carboxylic acid |
| Cetyl/Stearyl | 6 | Ceteareth-7 carboxylic acid |
| Lauryl | 16 | Laureth-1 7 carboxylic acid |
| Tallow | 6 | Talloweth-7 carboxylic acid |

Preferred sulfonates which could be a lubricant component according to the invention are those corresponding to the general formula VII:

wherein
$R^1$ is a $C_1$ to $C_{14}$ alkyl rest and if n>1, each $R^1$ can independently be a different $C_1$ to $C_{14}$ alkyl rest and
n=1 to 5.

As sulfonates with the general formula VII, which can be applied advantageously, can be mentioned among others: sodium xylenesulfonate or an alkyl benzenesulfonate.

The absorption spectra of a plurality of aqueous conveyor lubricants containing at least one of these lubricant components have been measured. The compositions of various aqueous conveyor lubricants A to K under examination can bee seen in Table 1:

TABLE 1

| Lubricant | Component 1 | Component 2 | Component 3 | Component 4 |
|---|---|---|---|---|
| A | — | 10% | — | — |
| B | — | 8% | — | — |
| C | 3.1% | 7% | — | — |
| D | — | 7.5% | — | — |
| E | 10% | — | — | 10% |
| F | 4% | 4% | — | — |
| G | 5% | — | — | 5% |
| H | 5% | 5% | — | — |
| I | — | 6% | — | 6% |
| J | — | 6% | 2% | 6% |
| K | — | 7% | 2% | 6% |

The numbered components are the same as referred to in the description of FIG. 1.

The lubricant G contains for example component 1 with a concentration of 5% and component 4 with a concentration of 5%.

All of the aqueous conveyor lubricants under examination showed an absorption maximum within the wavelength range from 200 nm to 300 nm, mostly in the region of 220 nm or 234 nm. The total absorption of each wavelength can be the result of the absorption by one component of the lubricant or by several components of the lubricant.

Figure 2:
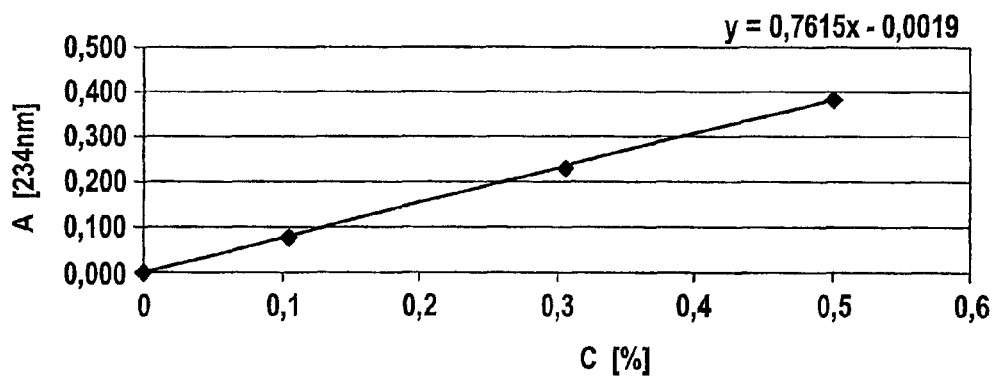
FIG. 2 shows a plot of absorbance versus concentration at one specific wavelength for a first aqueous conveyor lubricant.

FIG. 2 shows a plot of absorbance A versus concentration c at one specific wavelength for a first aqueous conveyor lubricant. This plot is a calibration curve, which can be used to determine the concentration of the lubricant after measuring the absorption of light at this specific wavelength by the lubricant.

In this case the aqueous conveyor lubricant was lubricant G of table 1. The absorbance A was measured at a wavelength $\lambda$ of 234 nm and with a path length d through the lubricant of 1 cm. The calibration curve shows a nice linearity of the absorbance as a function of the concentration. Therefore, a linear equation can be given (y=0.7615x−0.0019). With the help of this equation the concentration c (x) can be calculated from a measured absorbance A (y) for this lubricant, at this wavelength with the absorbance measured with the same set-up.

Figure 3:
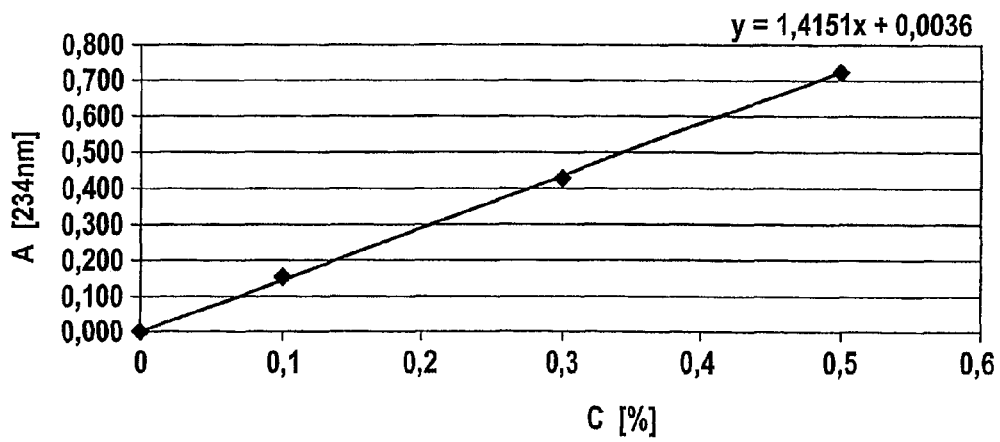
FIG. 3 shows a plot of absorbance versus concentration at one specific wavelength for a second aqueous conveyor lubricant.

FIG. 3 shows a plot of absorbance A versus concentration c at a wavelength $\lambda$ of 234 nm and with a path length d of 1 cm for a second aqueous conveyor lubricant. In this case, the lubricant was lubricant E from table 1.

Figure 4:
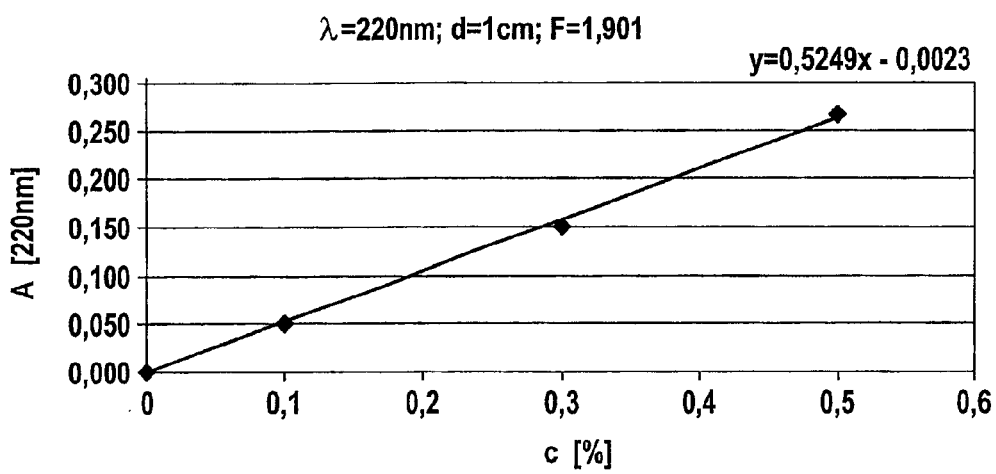
FIG. 4 shows a plot of absorbance versus concentration at one specific wavelength for a third aqueous conveyor lubricant.
Figure 5:
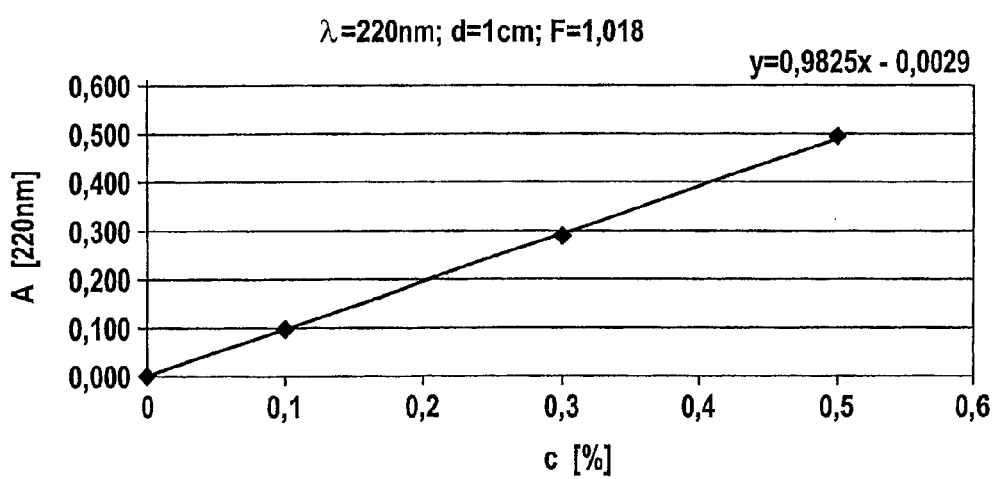
FIG. 5 shows a plot of absorbance versus concentration at one specific wavelength for a fourth aqueous conveyor lubricant.

FIGS. 4 and 5 show a plot of absorbance A versus concentration c at a wavelength $\lambda$ of 220 nm and with a path length d of 1 cm for a third an fourth aqueous conveyor lubricant, which were lubricants A and J respectively, according to table 1. All of the lubricants listed in table 1 showed a similar linear correlation of the absorbance and the concentration, all of the calibration curves being measured at 220 nm or 234 nm.

Furthermore, the influence of different water qualities (used for diluting the conveyor lubricant concentrates) and of product aging on the calibration curves was tested. Some of the calibration curves showed a minor dependency on these factors, which can be rated as being neglectable.

According to one embodiment of the present invention, the conveyor lubricant concentrate contains a tracer with a known concentration, the concentration of the aqueous conveyor lubricant being determined by measuring the absorption of light with a specific wavelength being absorbed primarily by the tracer. When the conveyor lubricant concentrate is diluted, the tracer (with a known starting concentration) is diluted to the same degree. The tracer shows an absorption peak at a known wavelength. By measuring the absorbance of the aqueous conveyor lubricant with the diluted tracer at this wavelength, the concentration of the tracer and consequently the concentration of the conveyor lubricant can be determined. The tracer to be used in this context must be homogeneously distributable within the aqueous conveyor lubricant.

Figure 6:
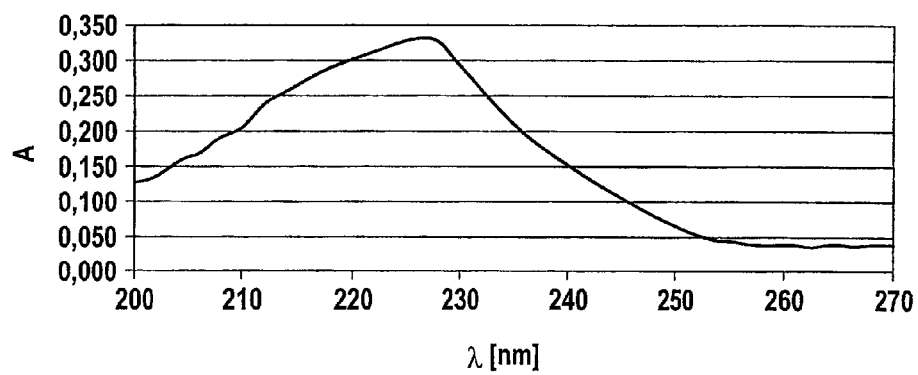
FIG. 6 shows an absorbance spectrum of a tracer, plotting absorbance versus wavelength.

FIG. 6 shows an absorbance spectrum of a tracer, plotting the absorbance A versus the wavelength $\lambda$. The tracer (0.5 mg/L) shows a maximum of absorption at a wavelength of about 228 m (path length d=1 cm). The tracer used was a naphtaline sulphone acid derivate, which is commercially available.

Figure 7:
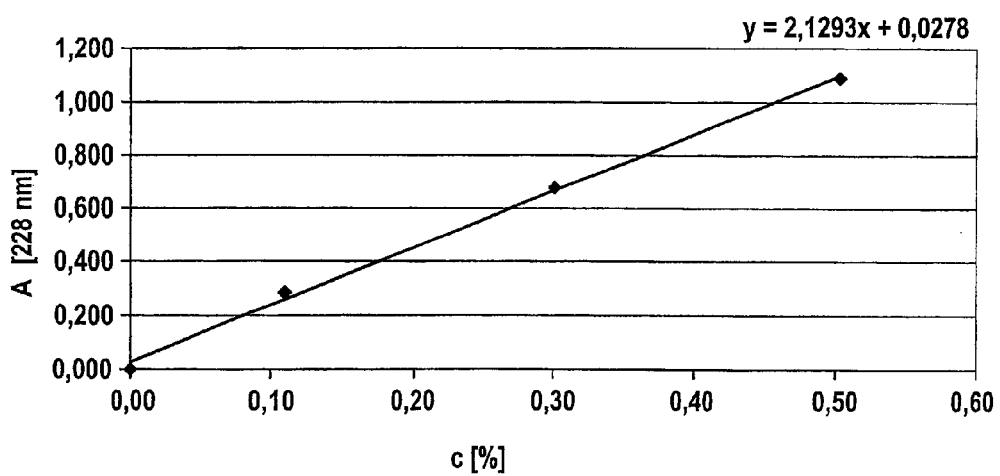
FIG. 7 shows a plot of absorbance versus concentration at one specific wavelength for the first aqueous conveyor lubricant of FIG. 2, to which a tracer has been added.

FIG. 7 shows a plot of absorbance versus concentration at a wavelength of 228 nm for the lubricant G (Table 1), to which the tracer (0.1% referring to the conveyor lubricant concentrate) has been added.

Figure 8:
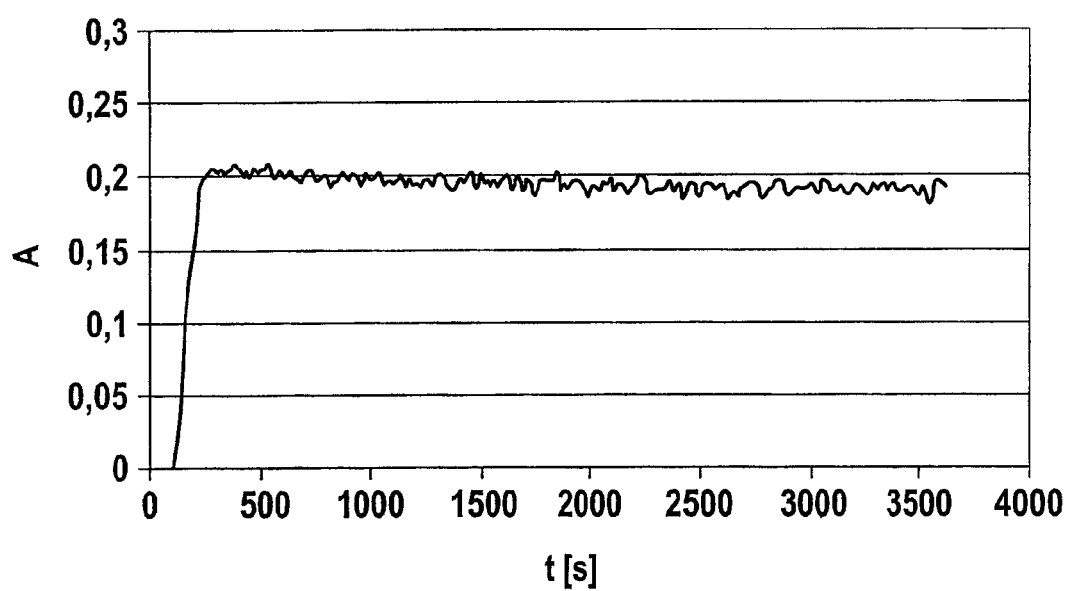
FIG. 8 is a plot of absorbance versus time, being the result of an on-line measurement at a conveyor lubrication system.

FIG. 8 is a plot of the absorbance A versus the time t, being the result of an on-line measurement at a conveyor lubrication system. The absorbance of the aqueous conveyor lubricant varies with time, which means, that the concentration of the lubricant also varies. By controlling the application quantity of lubricant applied to the conveyor system by the conveyor lubrication system depending upon the determined concentration, a constant lubrication can be assured, counteracting the variations of concentrations of the aqueous lubricant.

Figure 9:
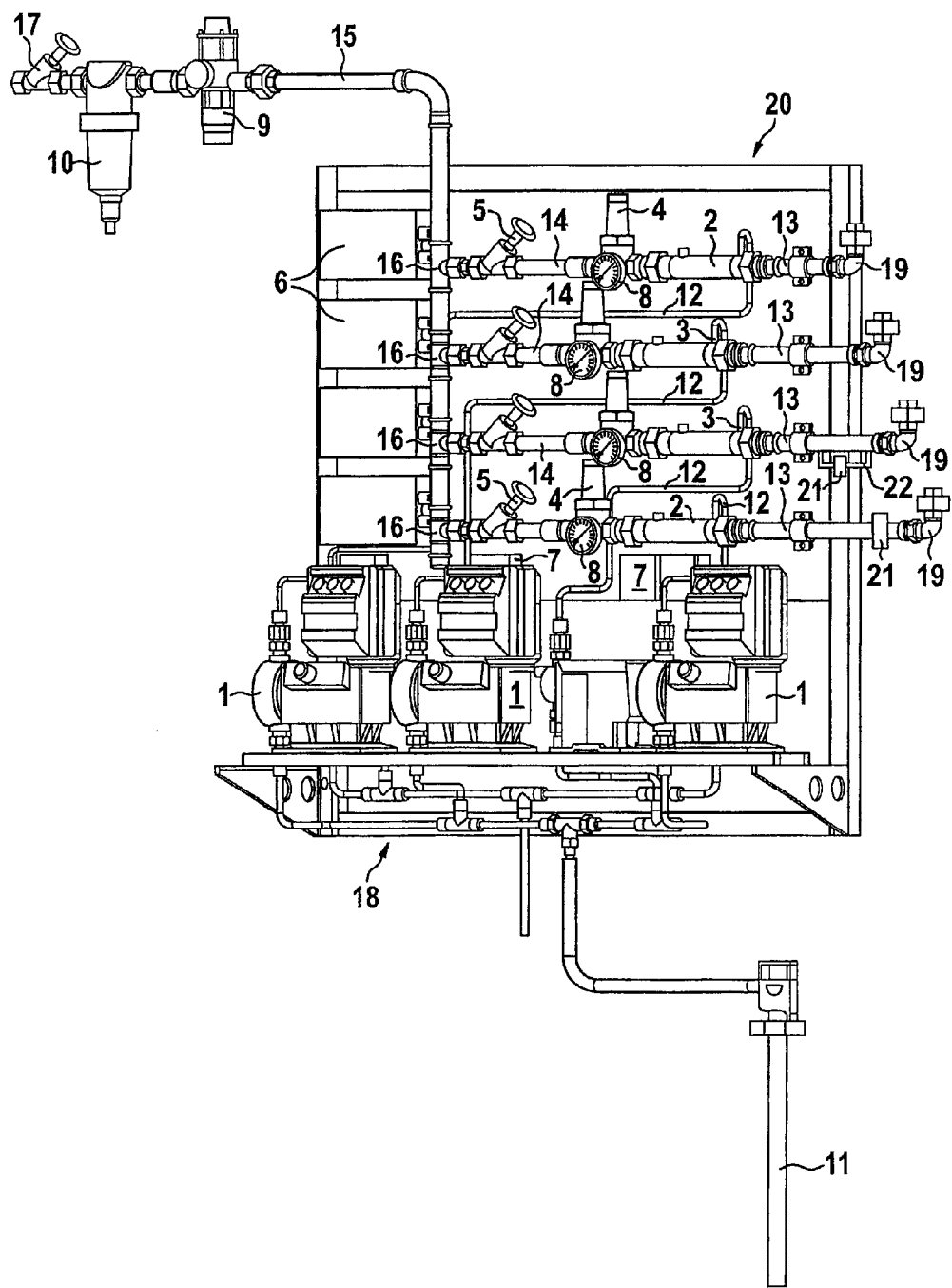
FIG. 9 shows schematically a dosing station, which is part of a conveyor lubrication system according to the present invention.

FIG. 9 shows schematically one embodiment of a dosing station, which is part of a conveyor lubrication system according to the present invention.

The dosing station 20 comprises dosing pumps 1 (attached to a power socket 7), which are connected to a suction pipe 11 via a pipe system 18. The suction pipe 1 is mounted within a tank (not shown) which contains a conveyor lubricant concentrate. The concentrate is pumped by the dosing pumps 1 through the suction pipe 11 via dosing pipes 12 into four different mixing spaces 13. The mixing spaces 13 are each attached to a water supply (not shown) the water being led through water pipes 14. The water pipes 14 are connected to a main water pipe 15. The main water pipe 15 further contains a main regulating valve 17, a water filter 10 and a disconnecting part 9. The main water pipe 15 meets the four water pipes 14 at the branching 16. Next to each branching 16 each water pipe 14 contains a regulating valve 5 and a pressure measuring device 8 with a pressure reducing regulator 4. Within each water pipe 14 a water meter 2 is installed. The water pipes 14 meet the dosing pipes 12 at dosing valves 3, which control the amount of conveyor lubricant concentrate to be added to the water. The lubricant concentrate and the water are mixed within the mixing spaces 13, obtaining an aqueous conveyor lubricant, which flows through outlet pipes 19 to the application device (not shown) for the application to a conveyor system. The electronical parts of the dosing station 20 are placed in housings 6. With the four different water pipes 14 and the four different dosing pipes 12, four different concentrations of the aqueous conveyor lubricant can be mixed and led to four different conveyor systems or alternately to one conveyor system.

The conveyor lubrication system further includes a measuring device 21, which is shown schematically in FIG. 9. The measuring device includes a light source and an absorption detector for measuring the absorption of light by the aqueous conveyor lubricant. The measuring device 21 can be positioned anywhere within the conveyor lubrication system, where the system contains the readily mixed aqueous conveyor lubricant (starting from the mixing spaces 13 and previous to the location where the lubricant is applied to the conveyor). The measuring device can be installed in such a way, that the aqueous conveyor lubricant flowing through the pipes of the system is measured directly within these pipes or that part of the aqueous conveyor lubricant is lead through a bypass, the lubricant being analyzed by the measuring device 21 within this bypass. By way of example the measuring device 21 is shown schematically in FIG. 9, attached to one outlet pipe 19, the aqueous conveyor lubricant being analyzed by the measuring device 21 within the outlet pipe 19 through light transmitting windows (e.g. of a flow cell), or attached to a bypass 22, the aqueous conveyor lubricant being analyzed by the measuring device 21 within the bypass 22 through light transmitting windows (e.g. of a flow cell).

The invention claimed is:
1. A method of lubricating a conveyor system comprising
   i) irradiating an aqueous conveyor lubricant having a concentration c with light, the aqueous conveyor lubricant comprising water and at least one lubricant component,
   ii) determining the concentration c of the aqueous conveyor lubricant by measuring the molecular absorption of the light by the aqueous conveyor lubricant with an absorption detector and
   iii) applying the aqueous conveyor lubricant to the conveyor system,
   wherein the concentration c is an amount of the aqueous conveyor lubricant per a unit amount of diluent water.

2. The method of claim 1 containing the step of diluting a conveyor lubricant concentrate with water to obtain the aqueous conveyor lubricant with the concentration c.

3. The method of claim 1, wherein the concentration c of the aqueous conveyor lubricant is determined by measuring the molecular absorption of ultraviolet light of a specific wavelength, the ultraviolet light being primarily absorbed by at least one lubricant component of the aqueous conveyor lubricant, the lubricant component being a component selected from the group of an amine, an ether carboxylic acid and a sulfonate.

4. The method of claim 1, wherein the molecular absorption of light with a wavelength in a range from 200 nm to 300 nm is measured.

5. The method of claim 1, wherein the molecular absorption of the light is measured online during operation of the conveyor system.

6. The method of claim 1, comprising controlling the application quantity of the aqueous conveyor lubricant depending on the determined concentration c.

7. The method of claim 2, wherein the conveyor lubricant concentrate contains a tracer with a known concentration, the concentration c of the aqueous conveyor lubricant being determined by measuring the molecular absorption of light with a specific wavelength being absorbed primarily by the tracer.

8. A conveyor lubrication system, including
i) an application device adapted to apply an aqueous conveyor lubricant to a conveyor system, the aqueous conveyor lubricant comprising water and at least one lubricant component,
ii) a measuring device coupled to the application device, the measuring device including a light source and an absorption detector adapted to measure the molecular absorption of light by the aqueous conveyor lubricant within the conveyor lubrication system, and
iii) a data processing unit coupled to the measuring device, the data processing unit adapted to determine a concentration c of the aqueous conveyor lubricant from the measured molecular absorption, wherein the concentration c is an amount of the aqueous conveyor lubricant per a unit amount of diluent water.

9. The conveyor lubrication system of claim 8, including a dosing station coupled to the application device, the dosing station containing at least one dosing pump for pumping a conveyor lubricant concentrate through a dosing pipe into at least one mixing space, the mixing space being attached to a water supply for diluting the conveyor lubricant concentrate with water within the mixing space to obtain the aqueous conveyor lubricant and the mixing space being attached to at least one outlet pipe for transporting the aqueous conveyor lubricant out of the mixing space, the outlet pipe leading to the application device for applying the aqueous conveyor lubricant to the conveyor system.

10. The conveyor lubrication system of claim 8, wherein the measuring device includes a flow cell, which is equipped with the light source and the absorption detector and which is connected to an element of the application device, the element containing the aqueous conveyor lubricant.

11. The conveyor lubrication system of claim 9, wherein the measuring device includes a flow cell, which is equipped with the light source and the absorption detector and which is connected to an element of the dosing station or the application device, the element containing the aqueous conveyor lubricant.

12. The method of claim 1, wherein the step of determining the concentration c further comprises comparing the measured molecular absorption to a calibration curve of the molecular absorption of the aqueous conveyor lubricant as a function of the concentration of the aqueous conveyor lubricant.

13. A method of lubricating a conveyor system comprising
i) irradiating an aqueous conveyor lubricant having a concentration c with light, the aqueous conveyor lubricant comprising water and at least one lubricant component,
ii) determining the concentration c of the aqueous conveyor lubricant by measuring the molecular absorption of the light by the aqueous conveyor lubricant with an absorption detector and
iii) applying the aqueous conveyor lubricant to the conveyor system,
wherein the concentration c is an amount of the aqueous conveyor lubricant per a unit amount of diluent water and further wherein the wavelength of light is selected to maximize the molecular absorption of the light by the aqueous conveyor lubricant.

14. The method of claim 13, wherein the wavelength of light is in a range from 200 nm to 300 nm.

15. The conveyor lubrication system of claim 8, wherein the data processing unit is adapted to compare the measured molecular absorption to a calibration curve of the molecular absorption of the aqueous conveyor lubricant as a function of the concentration of the aqueous conveyor lubricant.

16. A conveyor lubrication system, including
i) an application device adapted to apply an aqueous conveyor lubricant to a conveyor system, the aqueous conveyor lubricant comprising water and at least one lubricant component, and
ii) a measuring device coupled to the application device, the measuring device including a light source and an absorption detector adapted to measure the molecular absorption of light by the aqueous conveyor lubricant within the conveyor lubrication system,
wherein the wavelength of the light source is that which maximizes the molecular absorption of the light by the aqueous conveyor lubricant.

17. The conveyor lubrication system of claim 16, wherein the wavelength of the light source is in a range from 200 nm to 300 nm.

18. The conveyor lubrication system of claim 16, including a data processing unit coupled to the measuring device, the data processing unit adapted to determine a concentration c of the aqueous conveyor lubricant from the measured molecular absorption, wherein the concentration c is an amount of the aqueous conveyor lubricant per a unit amount of diluent water.

19. The method of claim 1, further wherein the determining step uses a measuring device and the applying step uses an application device and further wherein, the measuring device includes a flow cell, wherein the flow cell is equipped with a light source and the absorption detector and the flow cell is connected to an element of the application device, the element containing the aqueous conveyor lubricant, wherein the element is a pipe of the application device, through which the aqueous conveyor lubricant is flowing during the operation of the conveyor system.

20. The conveyor lubrication system of claim 11, wherein the element is a pipe of the dosing station or the application device, through which the aqueous conveyor lubricant is flowing during the operation of the conveyor lubrication system.

* * * * *